United States Patent
Humaydan

(10) Patent No.: US 9,516,827 B2
(45) Date of Patent: Dec. 13, 2016

(54) MELON VARIETY NUN 21267 MEM

(71) Applicant: Nunhems B.V., AC Nunhem (NL)

(72) Inventor: Hasib Humaydan, Acampo, CA (US)

(73) Assignee: Nunhems B.V., AB Nunhem (NL)

(*) Notice: Subject to any disclaimer, the term of this patent is extended or adjusted under 35 U.S.C. 154(b) by 0 days.

(21) Appl. No.: 14/621,816

(22) Filed: Feb. 13, 2015

(65) Prior Publication Data

US 2015/0156980 A1 Jun. 11, 2015

(51) Int. Cl.
*A01H 5/08* (2006.01)

(52) U.S. Cl.
CPC ...................................... *A01H 5/08* (2013.01)

(58) Field of Classification Search
None
See application file for complete search history.

(56) References Cited

U.S. PATENT DOCUMENTS

2006/0168701 A1  7/2006 Zhang et al.

FOREIGN PATENT DOCUMENTS

WO  2014076249 A1  5/2014

OTHER PUBLICATIONS

US Department of Agriculture, Agricultural Marketing Service, Plant Variety Protection Office, Beltsville, MD 20705, "Objective Description of Variety Muskmelon/Cantaloupe (Cucumis melo L.)" ams.usda.gov/AMSv1.0/getfile?dDocNanne=STELDEV3003780.
UPOV (International Union for the Protection of New Varieties of Plants), "Guidelines for the Conduct of Tests for Distinctness, Uniformity and Stability", TG/10415 (Geneva, 2006+2014) http://www.upov.int/edocs/tgdocs/en/tg104.pdf.
Wijnker et al, "Hybrid Recreation by Reverse Breeding in Arabidopsis thaliana", Nature Protocols, 2014, vol. 9, pp. 761-772 DOI: doi:10.1038/nprot.2014.049.
Brotman et al., "Resistance Gene Homologues in Melon are Linked to Genetic Loci Conferring Disease and Pest Resistance", Theor Appl Genet, 2002, vol. 104, pp. 1055-1063 DOI 10.1007/s00122-001-0808-x.
Colijn-Hooymans et al., "Competence for Regeneration of Cucumber Cotyledons is Restricted to Specific Developmental Stages", Plant Cell, Tissue and Organ Culture, 1994, vol. 39, pp. 211-217.
Ren et al., "Shoot Regeneration and Ploidy Variation in Tissue Culture of Honeydew Melon (Cucumis melo L. inodorus)", In Vitro Cell.Dev.Biol.—Plant, 2013, vol. 49, pp. 223-229 DOI 10.1007/s11627-012-9482-8.
Parvathaneni et al., "Fingerprinting in Cucumber and Melon (*Cucumis* spp.) Genotypes Using Morphological and ISSR Markers", J. Crop Sci. Biotech. 2011, vol. 1, pp. 39-43 DOI No. 10.1007/s12892-010-0080-1.
Vos et al., "AFLP: A New Technique for DNA Fingerprinting", Nucleic Acid Research, 1995, vol. 23, No. 21, pp. 4407-4414.
ACQUAAH, Principles of Plant Genetics and Breeding, 2007, Blackwell Publishing, ISBN-13: 978-1-4051-3646-4.

*Primary Examiner* — Brent Page

(57) ABSTRACT

The invention relates to the field of *Cucumis melo*, in particular to a new variety of melon designated NUN 21267 MEM as well as plants, seeds and melon fruits thereof.

18 Claims, No Drawings

MELON VARIETY NUN 21267 MEM

FIELD OF THE INVENTION

The present invention relates to the field of plant breeding and, more specifically, to the development of melon variety NUN 21267 MEM, also referred to as "NUN 21267", "NUN 21267 F1", "NUN 21267 hybrid", "21267 MEM" or "Silverock" and parts thereof and seeds from which the variety can be grown. The invention further relates to vegetative reproductions of NUN 21267 MEM, methods for in vitro tissue culture of NUN 21267 MEM explants and also to phenotypic variants of NUN 21267 MEM. The invention further relates to methods of producing fruits of NUN 21267 MEM or of phenotypic variants of NUN 21267 MEM.

The goal of vegetable breeding is to combine various desirable traits in a single variety/hybrid. Such desirable traits may include greater yield, resistance to insects or pests, tolerance to heat and drought, desired earliness, seedless fruits, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is the melon. It is a member of the Cucurbitacea family. The genus Cucumis melo originated in Africa. The plant is a large and sprawling annual, grown for its fruit. The fruit of most species of Cucumis melo is often coloured attractively, commonly red. Melon can contain black seeds, which are considered undesirable for certain uses.

Many different melon cultivars have been produced, and melon breeding efforts have been underway in many parts of the world. Some breeding objectives include varying the color, texture and flavor of the fruit, and absence of seeds. Other objectives include disease or pest resistance, optimizing flesh thickness, yield, suitability to various climatic circumstances, solid content (% dry matter), and sugar content.

Honeydew melons are part of the muskmelon cultivar group. They have a smooth rind, yellowish in color. They are usually mid-sized with oval shape. Honeydew grows best in semi-arid climates, and is grown and consumed all over the world. The flesh is thick, juicy and sweet, and can be green, white, cream, pale yellow or pale orange, and is very popular for use in desserts.

The new variety is a Honeydew type (*Cucumis melo inodorous*). It has a sparsely netted, yellow colored rind with pale yellow and green fruit flesh at edible maturity. NUN 21267 MEM has heavy fruits, with much high refractometer % of soluable solids and firmness. Fruit shape of NUN 21267 is oval. Provided are seeds of NUN 21267 MEM, plants and plant parts produced from these seeds such as harvested fruit or parts thereof, pollen, cells, leaves or parts thereof, petioles, shoots or parts thereof, stems or parts thereof, roots or parts thereof, cuttings or parts thereof, flowers, vegetative reproductions of the variety NUN 21267 MEM, and progeny of the variety.

SUMMARY OF THE INVENTION

In one aspect of the invention, a seed of melon variety NUN 21267 MEM is provided, wherein a representative sample of said seed has been deposited under Accession Number NCIMB 42626.

In another aspect the invention provides for a hybrid variety of *Cucumis melo* called NUN 21267 MEM. The invention also provides for a plurality of seeds of the new variety, plants produced from growing the seeds of the new variety NUN 21267 MEM, and progeny of any of these. Especially, progeny retaining one or more (or all) of the "distinguishing characteristics" or one or more (or all) of the "essential morphological and physiological characteristics" or essentially all physiological and morphological characteristics of NUN 21267 MEM referred to herein, are encompassed herein as well as methods for producing these.

In one aspect, such progeny have all the physiological and morphological characteristics of melon variety NUN 21267 MEM when grown under the same environmental conditions. In another aspect such progeny have all the physiological and morphological characteristics as listed in Table 1 as melon variety NUN 21267 MEM when measured under the same environmental conditions (i.e. evaluated at significance levels of 1%, 5% or 10% significance, which can also be expressed as a p value).

In another aspect a plant of the invention or said progeny plants has/have 1, 2, 3, 4 or more or all of the distinguishing characteristics selected from the group consisting of: 1) an average mature fruit diameter of about 16 cm, e.g. 14, 15, 16, 17 or 18 cm; 2) an average mature fruit weight of about 2873 g e.g. 2850, 2860, 2870, 2880 or 2890 gram; 3) an average maturity from seeding to harvest of about 88 days e.g. 86, 87, 88, 89 or 90 days from seeding; 4) an average mature fruit refractometer % soluble solids (center of flesh) of about 13.4 e.g. 11, 12, 13, 14, 15 or 16; 5) an average number of about 700 seeds per mature fruit e.g. about 670, 680, 690, 700, 710, 720, or 730 seeds; 6) an average weight per 1000 seeds of 39 g, e.g. 37, 38, 39, 40 or 41 gram; 7) an average rind thickness at medial of about 1.65 mm. e.g. 1.50, 1.60, 1.65, 1.70 or 1.80 mm; 8) sparse presence of rind net; 9) an average mature fruit length of about 19 cm, e.g. 17, 18, 19, 20 or 21 cm; and 10) an average fruit firmness of about 3.7 pound force, e.g. 3.3, 3.4, 3.5, 3.6, 3.7, 3.8, 3.9, 4.0 or 4.1 pound force. In another aspect a plant of the invention has in addition to the 1, 2, 3, 4 or more or all of the above-cited distinguishing characteristics, 3, 4, 5, 6, 7, 8, or more, or all of the other (average) characteristics as listed in Table 1.

Further, a melon fruit produced on a plant grown from these seeds is provided.

In yet another embodiment of the invention, a plant having one, two or three physiological and/or morphological characteristics which are different from those of NUN 21267 MEM and which otherwise has all the physiological and morphological characteristics of NUN 21267 MEM as listed in Table 1, wherein a representative sample of seed of variety NUN 21267 MEM has been deposited under Accession Number NCIMB 42626, is provided.

Further, a vegetatively propagated plant of variety NUN 21267 MEM, or a part thereof, is provided having all the morphological and physiological characteristics of NUN 21267 MEM when grown under the same environmental conditions.

Also a plant part derived from variety NUN 21267 MEM is provided, wherein said plant part is selected from the group consisting of: fruit, harvested fruit, parts of fruits, leaf, pollen, ovule, cell, part of a leaf, petioles, shoots or parts thereof, stems or parts thereof, vines or parts thereof, roots or parts thereof, cuttings, seeds, hypocotyl, cotyledon, flowers or parts thereof, scion, cion, stock, rootstock and flower. Fruits are particularly important plant parts.

DEFINITIONS

"Melon" or "muskmelon" refers herein to plants of the species *Cucumis melo*, and fruits thereof.

"Cultivated melon" refers to plants of *Cucumis melo* i.e. varieties, breeding lines or cultivars of the species *C. melo* as well as crossbreds thereof, or crossbreds with other *Cucumis melo* species, or even with other Cucurbitacea species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Cucumis melo* and related species.

"Netted" skin or rind refers to the presence of reticulate markings called 'netting' on the skin. "Non-netted" or "absence of netting" refers to the fruits lacking such netting. "Ribbed" refers to grooves and raised parts, running approximately straight and parallel from (near) blossom end to (near) abscission end that are called 'ribs'. "Non-ribbed" or "absence of ribbing" refers to the fruits lacking such ribs.

Refractometer % of soluble solids is the percentage of soluble solids in fruit juice, as defined by the USDA. It is also expressed as °Brix and indicates sweetness. The majority of soluble solids in melon are mainly sugars present in the fruits of melon. Hence the correlation with sweetness. Brix can be measured using a Brix meter (also known as Refractometer).

"Uniform throughout the fruit" or "uniform throughout the rind" refers to a characteristics such as color or absence of netting being identical throughout the entire fruit (e.g. throughout the fruit flesh when the fruit is cut in half) or rind.

The terms "melon plant designated NUN 21267 MEM", "NUN 26357" "26357 MEM" or "variety designated NUN 26357" are used interchangeably herein and refer to a melon plant of variety NUN 21267 MEM, representative seed of which having been deposited under Accession Number NCIMB 42626.

"Tissue culture" refers to a composition comprising isolated cells of the same or a different type or a collection of such cells organized into parts of a plant. Tissue culture of various tissues of melon and regeneration of plants therefrom is well known and widely published (see, e.g., Ren et al., In Vitro Cell. Dev. Biol.-Plant (2013) 49:223-229; Colijn-Hooymans (1994), Plant Cell, Tissue and Organ Culture 39: 211-217). Similarly, the skilled person is well-aware how to prepare a "cell culture".

"UPOV descriptors" are the plant variety descriptors described for melon in the "Guidelines for the Conduct of Tests for Distinctness, Uniformity and Stability, TG104/5 (Geneva, as last revised in 2014), as published by UPOV (International Union for the Protection of New Varieties and Plants, available on the world wide web at upov.int) and which can be downloaded from the world wide web at upov.int/under edocs/tgdocs/en/tg104.pdf and is herein incorporated by reference in its entirety.

"USDA descriptors" are the plant variety descriptors for melon (*Cucumis melo*) in the form titled "OBJECTIVE DESCRIPTION OF VARIETY—Muskmelon/Cantaloupe (*Cucumis melo* L.)" as published by the US Department of Agriculture, Agricultural Marketing Service, Plant Variety Protection Office, Beltsville, Md. 20705 and which can be downloaded from the world wide web at ams.usda.gov/under AMSv1.0/getfile?dDocName=STELDEV3003780.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8, D-97877 Wertheim, Article-No.: Art62-00008 EAN-Nr.: 4250193402112).

As used herein, the term "plant" includes the whole plant or any parts or derivatives thereof, preferably having the same genetic makeup as the plant from which it is obtained, such as plant organs (e.g. harvested or non-harvested fruits), plant cells, plant protoplasts, plant cell tissue cultures or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, clonally propagated plants, roots, stems, vines, root tips, grafts, scions, rootstocks, parts of any of these and the like. Also any developmental stage is included, such as seedlings, cuttings prior or after rooting, mature plants or leaves.

"Harvested plant material" refers herein to plant parts (e.g. fruits detached from the whole plant) which have been collected for further storage and/or further use.

"Harvested seeds" refers to seeds harvested from a line or variety, e.g. produced after self-fertilization or cross-fertilization and collected.

"Internode" refers to a portion of a plant stem or vine between nodes.

"Node" refers to the place on a plant stem or vine where a leaf is attached.

A plant having "all the physiological and morphological characteristics" of a referred-to-plant means a plant having the physiological and morphological characteristics of the referred-to-plant when grown under the same environmental conditions; the referred-to-plant can be a plant from which it was derived, e.g. the progenitor plant, the parent, the recurrent parent, the plant used for tissue- or cell culture, etc.

A plant having "essentially all the physiological and morphological characteristics" of a referred-to-plant means a plant having at least 5 (e.g. 6, 7, 8, 9 or all) of the distinguishing physiological and morphological characteristics (distinguishing characteristics as herein defined) when grown under the same environmental conditions of the referred-to-plant (e.g. a plant from which it was derived such as the progenitor plant, the parent, the recurrent parent, the plant used for tissue- or cell culture, etc.). Alternatively, a plant having "essentially all the physiological and morphological characteristics" of a referred-to-plant means a plant having all the characteristics as listed in Table 1 when grown under the same environmental conditions as a referred-to-plant (e.g. a plant from which it was derived such as the progenitor plant, the parent, the recurrent parent, the plant used for tissue- or cell culture, etc.). In another embodiment, a plant having "essentially all the physiological and morphological characteristics" of a referred-to-plant means a plant having all but 1, 2, 3, 4 or 5 of the characteristics as listed in Table 1 when grown under the same environmental conditions as a referred-to-plant (e.g. a plant from which it was derived such as the progenitor plant, the parent, the recurrent parent, the plant used for tissue- or cell culture, etc.).

For NUN 21267 MEM the distinguishing characteristics are 1) average mature fruit diameter; 2) average mature fruit weight; 3) average number of days to maturity from seeding to harvest; 4) average mature fruit refractometer % soluble solids (center of flesh); 5) average number of seeds per mature fruit; 6) average weight per 1000 seeds; 7) rind thickness at medial; 8) presence of rind net; 9) average mature fruit length and 10) average fruit firmness.

In certain embodiments the plant of the invention has all the physiological and morphological characteristics, except for certain characteristics mentioned, e.g. the characteristic(s) derived from a converted or introduced gene or trait and/or except for the characteristics which differ.

Similarity between different plants is defined as the number of distinguishing characteristics (or the characteristics as listed in Table 1) that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions.

A plant having one or more "essential physiological and/or morphological characteristics" or one or more "distinguishing characteristics" refers to a plant having (or retaining) one or more of the characteristics mentioned in Table 1 when grown under the same environmental conditions that distinguish NUN 21267 MEM from the most similar varieties (such as variety Santa Fe), such as but not limited to average number of fruits per plant, fruit flavor and texture, maturity, average flower diameter or average vine length.

"Distinguishing characteristics" or "distinguishing morphological and/or physiological characteristics" refers herein the characteristics which are distinguishing between NUN 21267 MEM and other melon varieties, such as Santa Fe, when grown under the same environmental conditions, especially the following characteristics 1) an average mature fruit diameter of about 15.9 cm (e.g. between 15.9−5% and 15.9+5%); 2) an average mature fruit weight of about 2873 gram (e.g. between 2873−5% and 2873+5%); 3) an average maturity from seeding to harvest of 88 days from seeding (e.g. between 88−5% and 88+5%); 4) an average mature fruit refractometer % soluble solids (center of flesh) of about 13.4 (e.g. between 13.4−5% and 13.4+5%); 5) an average of about 700 seeds per mature fruit (e.g. between 700−5% and 700+5%); 6) an average weight per 1000 seeds of about 39 gram (e.g. between 39−5% and 39+5%); 7) a rind thickness at medial of about 1.65 mm (e.g. between 1.65−5% and 1.65+5%); 8) sparse presence of rind net; 9)) an average mature fruit length of about 19 cm (e.g. between 19−5% and 19+5%) and 10) an average fruit firmness of about 3.7 pound force (e.g. between 3.7−5% or 3.7+5%). In one aspect, the distinguishing characteristics further include at least one, two, three or more (or all) of the characteristics listed in Table 1. All numerical distinguishing characteristics are statistically significantly different at $p \leq 0.05$.

Thus, a melon plant "comprising the distinguishing characteristics of NUN 21267 MEM" refers herein to a melon plant which does not differ significantly from NUN 21267 MEM in characteristics 1) to 5) above. In a further aspect the melon plant further does not differ significantly from NUN 21267 MEM in one or more, or all characteristics 6) to 10) as mentioned above. In yet a further aspect the melon plant further does not differ in at least one, two, three, four, five or six (or all) characteristics selected from the characteristics listed in Table 1. In still another aspect the melon plant does not differ in any of the distinguishing characteristics 1) to 10) listed above.

The physiological and/or morphological characteristics mentioned above are commonly evaluated at significance levels of 1%, 5% or 10% if they are numerical, or for identical type if not numerical, when measured under the same environmental conditions. For example, a progeny plant of NUN 21267 MEM may have one or more (or all) of the essential physiological and/or morphological characteristics of NUN 21267 MEM listed in Table 1, as determined at the 5% significance level (i.e. $p \leq 0.05$) when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Plant line" is for example a breeding line which can be used to develop one or more varieties. Progeny obtained by selfing a plant line has the same phenotype as its parents.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, vines, fruit, petiole, etc. When a whole plant is regenerated by vegetative propagation, it is also referred to as a vegetative propagation.

"Planting" or "planted" refers to seeding (direct sowing) or transplanting seedlings (plantlets) into a field by machine or hand.

"Yield" means the total weight of all melon fruits harvested per hectare of a particular line or variety. It is understood that "yield" expressed as weight of all melon fruits harvested per hectare can be obtained by multiplying the number of plants per hectare times the "yield per plant".

"Marketable yield" means the total weight of all marketable melon fruits harvested per hectare of a particular line or variety, i.e. fruits suitable for being sold for fresh consumption, having good flavor (no off-flavors), acceptable brix (or Total Soluble Solids, TSS, as determined using a refractometer) and flesh color properties and no or very low levels of deficiencies.

"Selfing" refers to self-pollination of a plant, i.e., the transfer of pollen from the anther to the stigma of the same plant. "Crossing" refers to the mating of two parent plants.

"Average" refers herein to the arithmetic mean.

"Substantially equivalent" refers to a characteristic that, when compared, does not show a statistically significant difference (e.g., p=0.05) from the mean. ANOVA is a suitable method for determining the value of p.

"Locus" (plural loci) refers to the specific location of a gene or DNA sequence on a chromosome. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Maturity" refers to the fruit developmental stage when the fruit has fully developed (reached its final size), begins to ripen and undergoes ripening, during which fruits can be divided into 1, 2, 3 or more maturity stages. Thereafter, fruits become overripe. In particular embodiments "maturity" is defined as the mature stage of fruit development and optimal time for harvest. In one embodiment a "mature" melon is defined as having reached the stage of maturity which will insure the proper completion of the normal ripening process. In particular embodiments, fruit should be harvested at a maturity stage i.e. substantially near maximum sweetness and flavor intensity.

"Harvest maturity" is referred to as the stage at which a melon fruit is ripe or ready for harvest or the optimal time to harvest the fruit. In one embodiment, harvest maturity is the stage which allows proper completion of the normal ripening.

"Flavor" refers to the sensory impression of a food or other substance, especially a melon fruit or fruit part (fruit flesh) and is determined mainly by the chemical senses of taste and smell. Flavor is influenced by texture properties and by volatile and/or non-volatile chemical components (organic acids, lipids, carbohydrates, etc.).

"Aroma" refers to smell (or odor) characteristics of melon fruits or fruit parts (fruit flesh).

"Cavity" or "seed cavity" is the center of the fruit containing the maternal tissues and seeds.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one melon line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated NUN 21267 MEM. Progeny may be derived by regeneration of cell culture or tissue culture or parts of a plant designated NUN 21267 MEM or selfing of a plant designated NUN 21267 MEM or by producing seeds of a plant designated NUN 21267 MEM. In further embodiments, progeny may also encompass plants derived from crossing of at least one plant designated NUN 21267 MEM with another melon plant of the same or another variety or (breeding) line, or wild melon plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to melon plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a melon variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a melon plant by transformation. A plant comprising a transgene stably integrated into its genome is referred to as "transgenic plant".

The term "mean" refers to the arithmetic mean of several measurements. The skilled person understands that the appearance of a plant depends to some extent on the growing conditions of said plant. Thus, the skilled person will know typical growing conditions for melons described herein. The mean, if not indicated otherwise within this application, refers to the arithmetic mean of measurements on at least 10 different, randomly selected plants of a variety or line.

"Substantially equivalent" refers to a characteristic that, when compared, does not show a statistically significant difference (e.g., p>0.05) from the mean.

DETAILED DESCRIPTION

The present invention relates to a *Cucumis melo* variety, referred to as NUN 21267 MEM, which—when compared to check variety Santa Fe—has higher average mature fruit weight, higher average mature fruit length, higher average mature fruit diameter, longer average time from seeding to maturity, higher average mature fruit rind thickness at medial, absence of rind net, higher average number of seeds per mature fruit, higher average leaf width, higher average mature fruit seed cavity length and lower average mature fruit seed cavity width. Also encompassed by the present invention are progeny plants having all but 1, 2, or 3 of the morphological and/or physiological characteristics of NUN 21267 MEM and methods of producing plants in accordance with the present invention.

A melon plant of NUN 21267 MEM differs from the most similar comparison variety Santa Fe in one or more characteristics (referred herein to as "distinguishing characteristics" or "distinguishing morphological and/or physiological characteristics" (or essential physiological and/or morphological characteristics) selected from:
1) NUN 21267 MEM has average mature fruit diameter that is at least 5%, e.g. 7, 8, 9, 10% or even about 10.4% higher than Santa Fe;
2) NUN 21267 MEM has an average mature fruit weight that is at least 15%, e.g. 25, 35, 40, 43% or even about 45% higher than Santa Fe;
3) NUN 21267 MEM has an average number of days to maturity from seeding to harvest that is at least 12%, e.g. 15, 18, 20, 22, 24, % or even 26% higher than Santa Fe;
4) NUN 21267 MEM has an average mature fruit refractometer % soluble solids (center of flesh) that is at least 40%, e.g. 50, 80, 100, 110, % or even about 120% higher than Santa Fe;
5) NUN 21267 MEM has an average number of seeds per mature fruit that is at least 5%, e.g. 6, 7, 7.5% or even about 8% lower than Santa Fe;
6) NUN 21267 MEM has an average weight per 1000 seeds that is at least 10%, e.g. 15, 20, 25, 28% or even about 30% higher than Santa Fe;
7) NUN 21267 MEM has an rind thickness at medial that is at least 20%, e.g. 25, 35, 40, 45% or even about 48% higher than Santa Fe;
8) NUN 21267 MEM sparse presence of rind net, whereas Santa Fe has absence of rind net;
9) NUN 21267 MEM has average mature fruit length that is at least 3%, e.g. 4, 5, 5.4% or even about 5.6% higher than Santa Fe; and
10) NUN 21267 MEM has an average fruit firmness that is at least 10%, e.g. 20, 25, 30, 35% or even about 40% lower than Santa Fe.

In another embodiment the plant of the invention is resistant to pests and diseases. On a scale of 1 to 9, where 1 is absence of resistance and 9 is highest resistance, NUN 21267 MEM has resistance to *Fusarium oxysporum* f.sp. *melonis* race 0 and race 2 that is 9 (resistance present). On a scale of 1 to 3, where 1 is absence of resistance and 3 is highest resistance, NUN 21267 MEM has resistance to Powdery mildew that is 2 (moderately resistant). On a scale of 1 to 3, where 1 is absence of resistance and 3 is highest resistance, NUN 21267 MEM has resistance to *Sphaerotheca fuliginea* race 0 and race 2 that is 2 (moderately resistant).

It is understood that "significant" differences refer to statistically significant differences, when comparing the characteristic between two plant lines or varieties when grown under the same conditions. Preferably at least about 10, 15, 20 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Thus, in one aspect, the invention provides seeds of the melon variety designated NUN 21267 MEM wherein a representative sample of seeds of said variety was deposited under the Budapest Treaty, with Accession number NCIMB 42626.

Seeds of NUN 21267 MEM are obtainable by crossing the male parent with the female parent and harvesting the seeds produced on the female parent. The resultant NUN 21267 MEM seeds can be grown to produce NUN 21267 MEM plants. In one embodiment a plurality of NUN 21267 MEM seeds are packaged into small and/or large containers (e.g., bags, cartons, cans, etc.). The seeds may be disinfected, primed and/or treated with various compounds, such as seed coatings or crop protection compounds.

Also provided are plants of melon variety NUN 21267 MEM, or a fruit or other plant part thereof, produced from seeds, wherein a representative sample of said seeds has been deposited under the Budapest Treaty, with Accession Number NCIMB 42626. Also included is a cell culture or tissue culture produced from such a plant. It is understood that such tissue or cell culture comprising cells or protoplasts from the plant of the invention can be obtained from a plant part selected from the group consisting of embryos, meristems, cotyledons, hypocotyl, pollen, leaves, anthers, roots, root tips, pistil, petiole, flower, fruit, seed, stem and stalks. In one embodiment a plant regenerated from such a cell or tissue culture said plant expressing all the morphological and physiological characteristics of NUN 21267 MEM.

In one embodiment the invention provides a melon plant regenerated from the tissue or cell culture of NUN 21267 MEM, wherein the plant has all of the physiological and morphological characteristics of NUN 21267 MEM as listed in Table 1 when determined at the 5% significance level. In another embodiment, the invention provides a melon plant regenerated from the tissue or cell culture of NUN 21267 MEM, wherein the plant has all of the physiological and morphological characteristics of NUN 21267 MEM when determined at the 5% significance level.

Plants of NUN 21267 MEM can be produced by seeding directly in the ground (e.g., field) or by germinating the seeds in controlled environment conditions (e.g., greenhouses) and then transplanting the seedlings into the field. For example, the seed can be sown into prepared seed beds where they will remain for the entire production of the crop. Alternatively, the melon seed may be planted or transplanted in prepared mounds.

In another aspect, the invention provides for a melon plant of variety NUN 21267 MEM, a representative sample of seed from said variety has been deposited under the Budapest Treaty, with Accession number NCIMB 42626.

In other aspects, the invention provides for a fruit or parts thereof of melon variety NUN 21267 MEM, or a plant part, such as pollen, flowers, shoots or cuttings of variety NUN 21267 MEM or parts thereof.

In one embodiment any plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated on the USDA Objective description of variety—Melon (unless indicated otherwise), when grown under the same environmental conditions):

1) NUN 21267 MEM has an average mature fruit diameter of about 15.9 cm e.g. between about 15 and about 17 cm or preferably between about 15.3 and about 16.6 cm or between about 15.6 and 16.2 cm or even between about 15.8 and 16.0 cm;

2) NUN 21267 MEM has an average mature fruit weight of about 2873 gram e.g. between about 2400 and about 3400 gram or preferably between about 2600 and about 3100 gram or between about 2800 and 2900 gram or even between about 2870 and 2880 gram;

3) NUN 21267 MEM has an average number of days to maturity from seeding to harvest of about 88 days from seeding e.g. between 82 and 94 or between 86 and about 90 or preferably between 87 and 89;

4) NUN 21267 MEM has an average mature fruit refractometer % soluble solids (center of flesh) of about 13.4 e.g. between 10 and 17 or preferably between 11 and 16 or between 12 and 15 or even between 13 and 14;

5) NUN 21267 MEM has an average number of seeds per mature fruit mature of about 700 e.g. between 500 and 900 or preferably between 600 and about 800 or between about 50 and 750 or even between about 680 and 720;

6) NUN 21267 MEM has an average weight per 1000 seeds of about 39 gram, e.g. between 33 and 45 or preferably between 35 and 43 or between 37 and 41 or even between 38 and 40 gram;

7) NUN 21267 MEM has an average rind thickness at medial of about 1.65 mm e.g. between 1.3 and 2.0 mm or preferably between 1.4 and 1.9 mm or between 1.5 and 1.8 mm or even between 1.6 and 1.7 mm;

8) NUN 21267 MEM has a sparsely present rind net;

9) NUN 21267 MEM has an average mature fruit length of about 19 cm e.g. between 17 and 21 cm or preferably between 18 and 20 cm or even between 18.5 and 19.5 cm; and 10) NUN 21267 MEM has an average fruit firmness of about 3.72 pound force ([lb/in$^2$]; 1 lb/in$^2$=70.31 g/cm$^2$) e.g. between 3 and 4.4 or preferably between 3.3 and 4.0 or even between 3.6 and 3.8 pound force.

In still another aspect the invention provides a method of producing a melon plant, comprising crossing a plant of melon variety NUN 21267 MEM with a second melon plant one or more times, and selecting progeny from said crossing.

In yet another aspect the invention provides a method of producing a melon plant, comprising selfing a plant of melon variety NUN 21267 MEM one or more times, and selecting progeny from said selfing.

In other aspects, the invention provides for progeny of variety NUN 21267 MEM such as progeny obtained by further breeding NUN 21267 MEM. Further breeding NUN 21267 MEM includes selfing NUN 21267 MEM one or more times and/or cross-pollinating NUN 21267 MEM with another melon plant or variety one or more times. In particular, the invention provides for progeny that retain all the essential morphological and physiological characteristics of NUN 21267 MEM or that retain one or more (e.g. 1) to 5) or 1) to 10) or all) of the distinguishing characteristics of the melon type described further above, or, in another embodiment, progeny that retain all morphological and physiological characteristics of NUN 21267 MEM as listed in Table 1; when grown under the same environmental conditions, when determined at the 5% significance level. In another aspect, the invention provides for vegetative reproductions of the variety and plants having all but 1, 2, or 3 of the physiological and morphological characteristics of NUN 21267 MEM (e.g. as listed in Table 1).

The morphological and/or physiological differences between plants according to the invention, i.e. NUN 21267 MEM or progeny thereof, or plants having all but 1, 2, or 3 of the physiological and morphological characteristics of NUN 21267 MEM (as listed in Table 1); and other known varieties can easily be established by growing NUN 21267 MEM next to the other varieties (in the same field, under the same environmental conditions), preferably in several locations which are suitable for said melon cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby maturity, ploidy, plant sex form, leaf shape, leaf color, stem shape, surface and length, flower size and color, fruit group, mature fruit color, fruit size, fruit shape, rind texture and thickness, flesh texture and color, disease resistance, insect resistance, can be measured and directly compared for species of *Cucumis melo*.

The morphological and physiological characteristics (and distinguishing characteristics) of NUN 21267 MEM, are provided in the Examples, in Table 1. Encompassed herein are also plants derivable from NUN 21267 MEM (e.g. by selfings and/or crossing and/or backcrossing with NUN 21267 MEM and/or progeny thereof) comprising all the physiological and morphological characteristics of NUN 21267 MEM listed in Table 1 as determined at the 5% significance level for numerical characteristics or identical for non-numerical characteristics when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of fruits can be compared, such as cold storage holding quality, post-harvest rind firmness and/or flesh firmness can be measured using known methods.

Flesh firmness can for example be measured using a penetrometer, e.g. by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, Va. 23502. For melons, it is preferably combined with a 8 mm round tip, also available from QA Supplies under #2006061-8.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World wide web at rhs.org.uk/Plants/RHS-Publications/RHS-colour-charts).

In a preferred embodiment, the invention provides for melon fruits of variety NUN 21267 MEM, or a part of the fruit. In another embodiment, the invention provides for a container comprising or consisting of a plurality of harvested melon fruits of NUN 21267 MEM, or progeny thereof, or a derived variety.

In yet a further embodiment, the invention provides for a method of producing a new melon plant. The method comprises crossing a plant of the invention NUN 21267 MEM, or a plant comprising all but 1, 2, or 3 of the morphological and physiological characteristics of NUN 21267 MEM (as listed in Table 1), or a progeny plant thereof, either as male or as female parent, with a second melon plant (or a wild relative of melon) one or more times, and/or selfing a melon plant according to the invention i.e. NUN 21267 MEM, or a progeny plant thereof, one or more times, and selecting progeny from said crossing and/or selfing. The second melon plant may for example be a line or variety of the species *Cucumis melo*, or other *Cucumis* species or even other Cucurbitacea species.

Progeny are a later generation (of seeds) produced from the first cross of the F1 hybrid with another plant (F2) or with itself (S2), or any further generation produced by crossing and/or selfing (F3, F4, etc.) and/or backcrossing (BC2, BC3, etc.) one or more selected plants of the F2 and/or S2 and/or BC2 generation (or plants of any further generation, e.g. the F3) with another melon plant (and/or with a wild relative of melon). Progeny may have all the physiological and morphological characteristics of melon variety NUN 21267 MEM when grown under the same environmental conditions and/or progeny may have (be selected for having) one or more of the distinguishing characteristics of melon of the invention. Using common breeding methods such as backcrossing or recurrent selection, one or more specific characteristics may be introduced into NUN 21267 MEM, to provide or a plant comprising all but 1, 2, or 3 or more of the morphological and physiological characteristics of NUN 21267 MEM (as listed in Table 1).

The invention provides for methods of producing plants which retain all the morphological and physiological characteristics of NUN 21267 MEM. The invention provides also for methods of producing a plant comprising all but 1, 2, or 3 or more of the morphological and physiological characteristics of NUN 21267 MEM (e.g. as listed in Table 1), but which are still genetically closely related to NUN 21267 MEM. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 21267 MEM if its DNA fingerprint is at least 80%, 90%, 95% or 98% identical to the fingerprint of NUN 21267 MEM. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1): 39-43). The invention also provides plants and varieties obtained by these methods. Plants may be produced by crossing and/or selfing, or alternatively, a plant may simply be identified and selected amongst NUN 21267 MEM plants, or progeny thereof, e.g. by identifying a variant within NUN 21267 MEM or progeny thereof (e.g. produced by selfing) which variant differs from NUN 21267 MEM in one, two or three of the morphological and/or physiological characteristics (e.g. in one, two or three distinguishing characteristics), e.g. those listed in Table 1 or others. In one embodiment the invention provides a melon plant having a Jaccard's Similarity index with NUN 21267 MEM of at least 0.8, e.g. at least 0.85, 0.9, 0.95, 0.98 or even at least 0.99.

By crossing and/or selfing also (one or more) single traits may be introduced into the variety of the invention i.e. NUN 21267 MEM (e.g., using backcrossing breeding schemes), while retaining the remaining morphological and physiological characteristics of NUN 21267 MEM and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 21267 MEM by breeding with NUN 21267 MEM.

Any pest or disease resistance genes may be introduced into a plant according to the invention, i.e. NUN 21267 MEM, progeny thereof or into a plant comprising all but 1, 2, or 3 or more of the morphological and physiological characteristics of NUN 21267 MEM (e.g. as listed in Table 1). Resistance to one or more of the following diseases or pests is preferably introduced into plants of the invention: Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* f.sp. *melonis* (Fom) race 0, *Fusarium oxysporum* f.sp. *melonis* (Fom) race 1, *Fusarium oxysporum* f.sp. *melonis* (Fom) race 2, *Fusarium oxysporum* f.sp. *melonis* (Fom) race 1-2, *Fusarium* Wilt R2, Anthracnose, Cucumber Mosaic, Squash Mosaic, Root Knot (Nematode), Aphid, Pickle Worm, Darkling Ground Beetle, Banded Cucumber Beetle, Mite, Western Spotted Cucumber Beetle, Melon Leafhopper, Melon Worm, Western Striped Cucumber Beetle and Melon Leafminer. Other resistance genes, against pathogenic viruses, fungi, bacteria, nematodes, insects or other pests may also be introduced.

Thus, invention also provides a method for developing a melon plant in a melon breeding program, using a melon plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 21267 MEM or progeny thereof, or a plant comprising all but 1, 2, or 3 or more of the morphological and physiological characteristics of NUN 21267 MEM (e.g. as listed in Table 1), with a different melon plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Brotman et al., Theor Appl Genet (2002) 104:1055-1063). For breeding methods in general see Principles of Plant Genetics and Breeding, 2007, George Acquaah, Blackwell Publishing, ISBN-13: 978-1-4051-3646-4.

The invention thus also provides a method of introducing a single locus conversion, or single trait conversion or introducing a desired trait, into a melon plant according to the invention and/or into NUN 21267 MEM comprising:
(a) crossing a melon plant of variety NUN 21267 MEM, a representative sample of seed of said variety having been deposited under Accession Number NCIMB 42626, with a second melon plant comprising a desired single locus to produce F1 progeny plants;
(b) selecting F1 progeny plants that have the single locus;

(c) crossing the selected progeny plants with a plant of NUN 21267 MEM, to produce backcross progeny plants;
(d) selecting backcross progeny plants that have the single locus and one or more (or all) distinguishing characteristics of melon according to the invention and/or all the physiological and morphological characteristics of NUN 21267 MEM to produce selected backcross progeny plants; and
(e) optionally repeating steps (c) and (d) one or more times in succession to produce selected second, third or fourth or higher backcross progeny plants that comprise the single locus and otherwise one or more (or all) the distinguishing characteristics of the melons according to the invention and/or comprise all of the physiological and morphological characteristics of NUN 21267 MEM, when grown in the same environmental conditions. The invention further relates to plants obtained by this method.

The above method is provided, wherein the single locus confers a trait, wherein the trait is pest resistance or disease resistance.

In one embodiment the trait is disease resistance and the resistance is conferred to Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* f.sp. *melonis* (Fom) race 0, *Fusarium oxysporum* f.sp. *melonis* (Fom) race 1, *Fusarium oxysporum* f.sp. *melonis* (Fom) race 2, *Fusarium oxysporum* f.sp. *melonis* (Fom) race 1-2, *Fusarium* Wilt R2, Anthracnose, Cucumber Mosaic, Squash Mosaic, Root Knot (Nematode), Aphid, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer.

The invention also provides a melon plant comprising at least a first set of the chromosomes of melon variety NUN 21267 MEM, a sample of seed of said variety having been deposited under Accession Number NCIMB 42626; optionally further comprising a single locus conversion, wherein said plant has essentially all of the morphological and physiological characteristics of the plant comprising at least a first set of the chromosomes of melon NUN 21267 MEM. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 21267 MEM may also be mutated (by e.g. irradiation, chemical mutagenesis, heat treatment, etc.) and mutated seeds or plants may be selected in order to change one or more characteristics of NUN 21267 MEM. Methods such as TILLING may be applied to melon populations in order to identify mutants. Similarly, NUN 21267 MEM may be transformed and regenerated, whereby one or more chimeric genes are introduced into the variety or into a plant comprising all but 1, 2, 3, or more of the morphological and physiological characteristics (e.g. as listed in Table 1). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 21267 MEM, or progeny thereof, by transforming NUN 21267 MEM or progeny thereof with a transgene that confers the desired trait, wherein the transformed plant retains all the phenotypic and/or morphological and/or physiological characteristics of NUN 21267 MEM or the progeny thereof and contains the desired trait.

The invention also provides for progeny of hybrid (F1) variety NUN 21267 MEM obtained by further breeding with NUN 21267 MEM. In one aspect progeny are F2 progeny obtained by crossing NUN 21267 MEM with another plant or S2 progeny obtained by selfing NUN 21267 MEM. Also encompassed are F3 progeny obtained by selfing the F2 plants. "Further breeding" encompasses traditional breeding (e.g., selfing, crossing, backcrossing), marker assisted breeding, and/or mutation breeding. In one embodiment, the progeny have one or more (or all) of the distinguishing characteristics mentioned further above when grown under the same environmental conditions. In a further embodiment the progeny have all the physiological and morphological characteristics of variety NUN 21267 MEM when grown under the same environmental conditions. In another embodiment the progeny have one, two, or three distinct traits (qualitative or quantitative) introduced into NUN 21267 MEM, while retaining all the other physiological and morphological characteristics of variety NUN 21267 MEM when grown under the same environmental conditions.

The invention also provides a plant having one, two or three physiological and/or morphological characteristics which are different from those of NUN 21267 MEM and which otherwise has all the physiological and morphological characteristics of NUN 21267 MEM, wherein a representative sample of seed of variety NUN 21267 MEM has been deposited under Accession Number NCIMB 42626. In particular plants which differ from NUN 21267 MEM in none, one, two or three of the characteristics mentioned in Table 1 are encompassed.

In one aspect, the plant having one, two or three physiological and/or morphological characteristics which are different from those of NUN 21267 MEM and which otherwise has all the physiological and morphological characteristics of NUN 21267 MEM differs from NUN 21267 MEM in one, two or three of the distinguishing morphological and/or physiological characteristics selected from 1) average mature fruit diameter; 2) average mature fruit weight; 3) average number of days to maturity from seeding to harvest; 4) average mature fruit refractometer % soluble solids (center of flesh); 5) average number of seeds per mature fruit; 6) average weight per 1000 seeds; 7) rind thickness at medial; 8) presence of rind net; 9) average mature fruit length and 10) average fruit firmness.

In another embodiment the plant having one, two or three physiological and/or morphological characteristics which are different from those of NUN 21267 MEM and which otherwise has all the physiological and morphological characteristics of NUN 21267 MEM differs from NUN 21267 MEM in one, two or three morphological or physiological characteristic other than the "distinguishing morphological and/or physiological characteristics" (or essential physiological and/or morphological characteristics) of NUN 21267 MEM selected from: 1) average mature fruit diameter; 2) average mature fruit weight; 3) average number of days to maturity from seeding to harvest; 4) average mature fruit refractometer % soluble solids (center of flesh); 5) average number of seeds per mature fruit; 6) average weight per 1000 seeds; 7) rind thickness at medial; 8) presence of rind net; 9) average mature fruit length and 10) average fruit firmness.

Melons according to the invention, such as the variety NUN 21267 MEM, or its progeny, or a plant having all physiological and/or morphological characteristics but one, two or three which are different from those of NUN 21267

MEM, can also be reproduced using vegetative reproduction methods. Therefore, the invention provides for a method of producing plants, or a part thereof, of variety NUN 21267 MEM, comprising vegetative propagation of variety NUN 21267 MEM. Vegetative propagation comprises regenerating a whole plant from a plant part of variety NUN 21267 MEM (or from its progeny or from or a plant having all physiological and/or morphological characteristics but one, two or three, which are different from those of NUN 21267 MEM), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets.

The invention also provides for a vegetatively propagated plant of variety NUN 21267 MEM (or from its progeny or from or a plant having all but one, two or three physiological and/or morphological characteristics which are different from those of NUN 21267 MEM, or a part thereof, having one or more distinguishing characteristics and/or all the morphological and physiological characteristics of NUN 21267 MEM (except for the characteristics differing), when grown under the same environmental conditions.

Parts of NUN 21267 MEM (or of its progeny or of a plant having all physiological and/or morphological characteristics but one, two or three which are different from those of NUN 21267 MEM) encompass any cells, tissues, organs obtainable from the seedlings or plants, such as but not limited to: melon fruits or parts thereof, cuttings, hypocotyl, cotyledon, pollen, scion and the like. Such parts can be stored and/or processed further. Encompassed are therefore also food or feed products comprising one or more of such parts, such as canned, chopped, cooked, roasted, preserved, frozen, dried, pickled, or juiced melon fruit from NUN 21267 MEM or from progeny thereof, or from a derived variety, such as a plant having all but one, two or three physiological and/or morphological characteristics which are different from those of NUN 21267 MEM.

In one aspect haploid plants and/or double haploid plants of NUN 21267 MEM, or a plant having all but one, two or three physiological and/or morphological characteristics which are different from those of NUN 21267 MEM, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 21267 MEM (or from its progeny or from a plant having all but one, two or three physiological and/or morphological characteristics which are different from those of NUN 21267 MEM), or from a vegetatively propagated plant of NUN 21267 MEM (or from its progeny or from a plant having all but one, two or three physiological and/or morphological characteristics which are different from those of NUN 21267 MEM), being selected from the group consisting of: harvested fruits or parts thereof, pollen, cells, leaves or parts thereof, petioles, cotyledons, hypocotyls, shoots or parts thereof, stems or parts thereof, or vines or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising detecting in the genome (e.g., a sample of nucleic acids) of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a melon fruit or part thereof and/or an extract from a fruit or another plant part described herein. The food or feed product may be fresh or processed, e.g., dried, grinded, powdered, pickled, chopped, cooked, juiced, preserved, pickled, or powdered canned, steamed, boiled, blanched and/or frozen, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable melon fruits are generally sorted by size and quality after harvest. Alternatively the melon fruits can be sorted by Brix or sugar content.

Melons may also be grown for use in grafting or inosculation as rootstocks (stocks) or scions (scions). Typically, different types of melons are grafted to enhance disease resistance, which is usually conferred by the rootstock, while retaining the horticultural qualities usually conferred by the scion. It is not uncommon for grafting to occur between cultivated melon varieties and related Cucurbitae species. Methods of grafting and vegetative propagation are well-known in the art.

So in one aspect the invention relates to a plant comprising a rootstock or scion of NUN 21267 MEM.

Using methods known in the art like "reverse breeding", it is possible to produce parental lines for a hybrid plant such as NUN 21267 MEM; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Wijnker et al, Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 21267 MEM) comprising the step of making double haploid cells from haploid cells from the plant of the invention (NUN 21267 MEM) or a seed of that plant; and optionally crossing these parental lines to produce and collect seeds. In another aspect, the invention relates to a combination of parental lines produced by this method. In still another aspect said combination of parental lines can be used to produce a seed or plant of NUN 21267 MEM when these parental lines are crossed. In still another aspect, the invention relates to a combination of parental lines from which a seed or plant having all but one, two or three physiological and/or morphological characteristics of NUN 21267 MEM can be produced; or in another aspect, wherein a seed or plant having the distinguishing characteristics 1)-5) or 1)-10) of NUN 21267 MEM, as herein defined, can be produced when grown under the same environmental conditions. In still another aspect, the invention relates to a combination of parental lines from which a seed or plant having all the characteristics of NUN 21267 MEM as defined in Table 1 can be produced when grown under the same conditions.

All documents (e.g., patent publications) are herein incorporated by reference in their entirety.

CITED REFERENCES ams.usda.gov/AMSv1.0/getfile?dDocName=STELDEV3003780
http://www.rhs.org.uk/Plants/RHS-Publications/RHS-colour-charts
http://www.upov.int/edocs/tgdocs/en/tg076.pdf
Acquaah, Principles of Plant Genetics and Breeding, 2007, Blackwell Publishing, ISBN-13: 978-1-4051-3646-4
Brotman et al., Theor Appl Genet (2002) 104:1055-1063 DOI 10.1007/s00122-001-0808-x
Colijn-Hooymans (1994), Plant Cell, Tissue and Organ Culture 39: 211-217)
Ren et al., In Vitro Cell. Dev. Biol.-Plant (2013) 49:223-229 DOI 10.1007/s11627-012-9482-8;
Parvathaneni et al., J. Crop Sci. Biotech. 2011 (March) 14 (1): 39~43 DOI No. 10.1007/s12892-010-0080-1
Vos et al. 1995, Nucleic Acid Research 23: 4407-4414
Wijnker et al, Nature Protocols Volume: 9, Pages: 761-772 (2014) DOI:
doi:10.1038/nprot.2014.049
US 2006/0168701
WO2014076249

EXAMPLES

Development of NUN 21267 MEM

The hybrid NUN 21267 MEM was developed from a male and female proprietary inbred line of Nunhems. The female and male parents were crossed to produce hybrid (F1) seeds of NUN 21267 MEM. The seeds of NUN 21267 MEM can be grown to produce hybrid plants and parts thereof (e.g. melon fruit). The hybrid NUN 21267 MEM can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 21267 MEM is uniform and stable.

Deposit Information

A total of 2500 seeds of the hybrid variety NUN 21267 MEM were deposited according to the Budapest Treaty by Nunhems B.V. on Aug. 17, 2016, at or at the NCIMB Ltd., Ferguson Building, Craibstone Estate, Bucksburn, Aberdeen AB21 9YA, United Kingdom (NCIMB). The deposit has been assigned or NCIMB 42626. A deposit of NUN 21267 MEM and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808 (b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

"USDA descriptors" are the plant variety descriptors for melon (Cucumis melo)—Exhibit C of the U.S. Department of Agriculture, Agricultural Marketing Service, Science and Technology, Plant Variety Protection Office, Beltsville, Md. 20705, which can be downloaded from the world wide web at ams.usda.gov/AMSv1.0/getfile?dDocName=STELDEV3003780 and which is herein incorporated by reference in its entirety.

The most similar variety to NUN 21267 MEM is Santa Fe, a commercial variety from Seminis. In Table 1 a comparison between NUN 21267 MEM and Santa Fe is shown based on a trial in the USA. Trial location: Acampo Calif. USA, (coordinates: 38.192873°N, −121.232637°W). Sowing date: Jun. 12, 2014, transplanting date Jul. 10, 2014, harvesting date for NUN 21267 was Sep. 28, 2014.

Two replications of 50 plants each, from which 15 plants or plant parts were randomly selected to measure characteristics. In Table 1 the USDA descriptors of NUN 21267 MEM (this application) and reference Santa Fe (commercial variety) are summarized.

TABLE 1

| USDA Descriptor | Application Variety NUN 21267 MEM | Comparison Variety Santa Fe |
|---|---|---|
| 1. TYPE: 1 = Persian 2 = Honey Dew 3 = Casaba 4 = Crenshaw 5 = Common/Summer 6 = Other | 2 | 2 |

TABLE 1-continued

| USDA Descriptor | Application Variety NUN 21267 MEM | Comparison Variety Santa Fe |
|---|---|---|
| 2. AREA OF BEST ADAPTATION IN U.S.A.: 1 = Southeast 2 = Northeast/North Central 3 = Southwest 4 = Most Areas | 4 | 4 |
| 3. MATURITY: Days From Seeding to Harvest | 88 | 65-70 |
| 4. PLANT: | | |
| Fertility: 1 = Andromonoecious 2 = Monoecious 3 = Gynoecious 4 = Other | 1 | 1 |
| Habit: 1 = Vine 2 = Semi-bush 3 = Bush | 1 | 1 |
| 5. LEAF: | (Mature Blade of Third Leaf) | |
| Shape: 1 = Orbicular 2 = Ovate 3 = Reniform (Cordate) | 3 | 3 |
| Lobes: 1 = Not Lobed 2 = Shallowly Lobed 3 = Deeply Lobed | 2 | 2 |
| Color: 1 = Light Green (Honey Dew) 2 = Medium Green 3 = Dark Green (Rio Gold) | 1 | 1 |
| Color Chart Name | RHS | RHS |
| Color Chart Code | Green N137A | Green 137B |
| Average Length mm | n.r. | 164.8 |
| Average Width mm | n.r. | 178.7 |
| Surface: 1 = Pubescent 2 = Glabrous 3 = Scabrous | 3 | 3 |
| 6. FRUIT: | (at Edible Maturity): | |
| Average Length in cm | 19 | 18 |
| Average Diameter in cm | 15.9 | 14.4 |
| Average Weight in gram | 2873 | 1981.5 |
| Shape: 1 = Oblate 2 = Oval 3 = Round 4 = Elongate-Cylindrical 5 = Spindle 6 = Acorn | 2 | 2 |
| Surface: 1 = Smooth 2 = Netted 3 = Corrugated 4 = Warted | 1 + 2 | 1 |
| Blossom Scar: 1 = Obscure 2 = Conspicuous | 1 | 1 |
| Blossom diameter mm | 20.3 | 17.3 |
| Rib Presence: 1 = Absent 2 = Present | 1 | 1 |
| No. Ribs per Fruit | NA | NA |
| Rib Width at Medial in mm | NA | NA |
| Ribs Surface: 1 = Smooth 2 = Netted | NA | NA |
| Suture Depth: 1 = Shallow (Golden Delight) 2 = Medium 3 = Deep (Hackensack) | NA | NA |
| Suture Surface: 1 = Smooth 2 = Netted | NA | NA |
| Shipping Quality: 1 = Poor (Home Garden) 2 = Fair (Short Distance Shipping) 3 = Excellent (Long Distance Shipping) | 2 | n.r. |
| Fruit Abscission: 1 = When Ripe 2 = When Overripe 3 = Do Not Abscise | 3 | 3 |
| 7. RIND NET: | | |
| Net Presence: 1 = Absent 2 = Sparse 3 = Abundant | 2 | 1 |
| Distribution: 1 = Spotty 2 = Covers Entire Fruit | 1 | NA |
| Coarseness: 1 = Fine 2 = Medium Coarse 3 = Very Coarse | 1 | NA |
| Interlacing: 1 = None 2 = Some 3 = Complete | 1 | NA |
| Interstices: 1 = Shallow 2 = Medium Deep 3 = Deep | 1 | NA |
| 8. RIND TEXTURE: | | |
| Texture: 1 = Soft 2 = Firm 3 = Hard | 2 | 2 |
| Average Thickness at Medial in mm | 1.65 | 1.11 |

TABLE 1-continued

| USDA Descriptor | Application Variety NUN 21267 MEM | Comparison Variety Santa Fe |
|---|---|---|
| 9. RIND COLOR: Color Chart Name RHS | 01 = White 02 = Cream 03 = Buff 04 = Yellow 05 = Gold 06 = Green 07 = Orange 08 = Bronze 09 = Brown 10 = Gray 11 = Black 12 = Other (Specify) | |
| Rind Color At Edible Maturity | | |
| Primary Color/ | 02 | 06/01 |
| Color Chart Value | 10D (Yellow Green) | Green White 157B |
| Mottling Color/ | N.A. | N.A. |
| Color Chart Value | | |
| Net Color/ | 03 | N.A. |
| Color Chart Value | 161 (Greyed Yellow) | |
| Furrow (Suture)/ | N.A. | N.A. |
| Color Chart Value | | |
| Rind Color At Full Maturity | | |
| Primary Color/ | 04 | 04 |
| Color Chart Value | 7A (Yellow Green) | Yellow 7A |
| Mottling Color/ | N.A. | NA |
| Color Chart Value | | |
| Net Color/ | 03 | NA |
| Color Chart Value | 161C (Greyed Yellow) | |
| Furrow (Suture)/ | N.A. | NA |
| Color Chart Value | | |
| 10. FLESH (At Edible Maturity): Color Chart Name RHS | 01 = White 02 = Cream 03 = Yellow 04 = Green 05 = Orange 06 = Salmon 07 = Pink 08 = Other (Specify) | |
| Color Near Cavity/ | 01 | 01/04 |
| Color Chart Value | 155A (White) | NN155A (White green) |
| Color in Center/ | 04 | 01/04 |
| Color Chart Value | N144D (Yellow Green) | 143C (Green) |
| Color Near Rind/ | 03 | 03 |
| Color Chart Value | 160B (Greyed Yellow) | 160B (Greyed Yellow) |
| Refractometer % Soluable Solids (Center of Flesh) | 13.4 | 6.1 |
| Aroma: 1 = Absent 2 = Faint 3 = Strong | 2 | 2 |
| Flavor: 1 = Mild 2 = Somewhat Spicy 3 = Very Spicy | 2 | 2 |
| 11. SEED CAVITY: | | |
| Average Length in mm | 121.7 | 116.6 |
| Average Width in mm | 65.3 | 67.3 |
| Shape in X-Section: 1 = Circular 2 = Triangular | 2 | 2 |
| 12. SEEDS: | | |
| Average No. Seeds per Fruit | 700 | 761 |
| Average grams per 1,000 Seeds | 39 | 30 |

These are typical values. Values may vary due to environment. Other values that are substantially equivalent are also within the scope of the invention.
N.A. = not applicable;
n.r. = not recorded.

In one embodiment, the blossom scar of NUN 21267 MEM is 20.3 mm in diameter, whereas the blossom scar of Santa Fe is 17.3 mm in diameter. In still another embodiment, the average flesh firmness of NUN 21267 MEM is 3.72 pound force, whereas the average flesh firmness of Santa Fe is 6.22 pound force (measured by FT 327 Penetrometer using a 8 mm round tip).

The invention claimed is:

1. A plant, plant part or seed of melon variety NUN 21267 MEM, wherein a representative sample of said seed has been deposited under Accession Number NCIMB 42626.

2. A plant or part thereof grown from the seed of claim 1.

3. The plant part of claim 2, further defined as a leaf, pollen, stem, an ovule, a fruit, a scion, a rootstock, cutting, flower or a part of any of these or a cell.

4. A tissue or cell culture of regenerable cells of the plant of claim 2.

5. The tissue or cell culture according to claim 4, comprising cells or protoplasts from a plant part selected from the group consisting of embryos, meristems, cotyledons, hypocotyl, pollen, leaves, anthers, roots, root tips, pistil, petiole, flower, fruit, seed, stem and stalks.

6. A melon plant regenerated from the tissue or cell culture of claim 4, wherein the plant has all of the physiological and morphological characteristics of the plant of claim 2 as listed in Table 1, where numerical values are determined at the 5% significance level.

7. A method of producing of the plant of claim 2, or a part thereof, comprising vegetative propagation of the plant of claim 2.

8. The method of claim 7, wherein said vegetative propagation comprises regenerating a whole plant from a part of the plant of claim 2.

9. The method of claim 7, wherein said part is a cutting, a cell culture or a tissue culture.

10. A vegetative propagated plant of claim 2, or a part thereof, wherein the plant has all of the physiological and morphological characteristics of the plant of claim 2 when determined at the 5% significance level.

11. A method of producing a melon plant, comprising crossing the plant of claim 2 with a second melon plant one or more times.

12. The method of claim 11 further comprising a step of selecting progeny from said crossing.

13. The method of claim 12 further comprising a step of allowing the progeny to form seed.

14. A melon plant having one, two or three physiological and/or morphological characteristics which are different from those of the plant of claim 2 and which otherwise has all the physiological and morphological characteristics of the plant of claim 2 as listed in Table 1, when determined at the 5% significance level.

15. A food or feed product comprising the plant part of claim 3 wherein the plant part can be identified as a part of the plant of the invention.

16. The plant of claim 2 further comprising a single locus conversion, wherein said plant has all or all but one, two or three of the morphological and physiological characteristics of the plant of claim 2, optionally wherein the single locus conversion confers a trait selected from the group consisting of male sterility, herbicide tolerance, insect resistance, pest resistance, disease resistance, environmental stress tolerance, modified carbohydrate metabolism and modified protein metabolism.

17. A plant comprising the scion or rootstock of claim 3.

18. A method of producing a combination of parental lines of the plant of claim 2 comprising the step of making double haploid cells from haploid cells from the plant of claim 2 or a seed of claim 1.

\* \* \* \* \*